United States Patent
Vayser

(10) Patent No.: US 10,463,443 B2
(45) Date of Patent: Nov. 5, 2019

(54) SYSTEMS AND METHODS FOR ILLUMINATING AND IMAGING

(71) Applicant: Invuity, Inc., San Francisco, CA (US)

(72) Inventor: Alex Vayser, Mission Viejo, CA (US)

(73) Assignee: Invuity, Inc., San Francisco, CA (US)

( * ) Notice: Subject to any disclaimer, the term of this patent is extended or adjusted under 35 U.S.C. 154(b) by 154 days.

(21) Appl. No.: 15/434,546

(22) Filed: Feb. 16, 2017

(65) Prior Publication Data

US 2017/0231712 A1 Aug. 17, 2017

Related U.S. Application Data

(60) Provisional application No. 62/296,511, filed on Feb. 17, 2016.

(51) Int. Cl.

| | |
|---|---|
| *A61B 90/30* | (2016.01) |
| *H04N 5/225* | (2006.01) |
| *A61B 90/00* | (2016.01) |
| *A61B 90/20* | (2016.01) |
| *F21V 8/00* | (2006.01) |
| *A61B 1/06* | (2006.01) |
| *A61B 1/07* | (2006.01) |

(Continued)

(52) U.S. Cl.
CPC ............ *A61B 90/30* (2016.02); *A61B 1/0607* (2013.01); *A61B 1/0638* (2013.01); *A61B 1/0669* (2013.01); *A61B 1/07* (2013.01); *A61B 5/0059* (2013.01); *A61B 5/0077* (2013.01); *A61B 90/20* (2016.02); *A61B 90/361* (2016.02); *G02B 6/0008* (2013.01); *H04N 5/2256* (2013.01); *A61B 2090/306* (2016.02); *G02B 6/0028* (2013.01); *G02B 6/0045* (2013.01); *G02B 21/0012* (2013.01); *G02B 21/082* (2013.01); *G02B 23/2469* (2013.01); *G02B 27/48* (2013.01); *H04N 2005/2255* (2013.01)

(58) Field of Classification Search
CPC ....... A61B 90/30; A61B 90/20; A61B 90/361; A61B 1/04; A61B 2090/306; G02B 6/0008; G02B 23/2469; G02B 6/0028; G02B 6/0045; G02B 21/0012; G02B 21/082; G02B 27/48; H04N 2005/2255; H04N 5/2256
See application file for complete search history.

(56) References Cited

U.S. PATENT DOCUMENTS

| | | | |
|---|---|---|---|
| 5,305,121 A | 4/1994 | Moll | |
| 6,633,328 B1 * | 10/2003 | Byrd | H04N 7/183 348/143 |

(Continued)

FOREIGN PATENT DOCUMENTS

WO   WO-2014197241 A1   12/2014

OTHER PUBLICATIONS

International search report with written opinion dated May 5, 2017 for PCT/US2017/018156.

*Primary Examiner* — Huy T Nguyen

(74) *Attorney, Agent, or Firm* — McDonnell Boehnen Hulbert & Berghoff LLP

(57) ABSTRACT

A system for illuminating a surgical field comprises a surgical imaging element and an illumination element. The surgical imaging element images the surgical field and has an image axis. The illumination element or the imaging element may be moved independently of the other in order to control illumination or field of view.

40 Claims, 6 Drawing Sheets

(51) Int. Cl.
   *A61B 5/00*    (2006.01)
   *G02B 23/24*   (2006.01)
   *G02B 27/48*   (2006.01)
   *G02B 21/00*   (2006.01)
   *G02B 21/08*   (2006.01)

(56) References Cited

U.S. PATENT DOCUMENTS

| | | |
|---|---|---|
| 9,055,962 B2 | 6/2015 | Blumenkranz et al. |
| 2008/0058592 A1 | 3/2008 | Jones |
| 2012/0123212 A1 | 5/2012 | Dahmen et al. |
| 2013/0006052 A1 | 1/2013 | Song |
| 2013/0113909 A1* | 5/2013 | DeLand ............. A61B 50/28 348/77 |
| 2013/0292571 A1 | 11/2013 | Mukherjee et al. |
| 2014/0121459 A1* | 5/2014 | Hoeg ............. A61B 1/00179 600/109 |
| 2015/0173596 A1 | 6/2015 | Vayser |
| 2015/0381909 A1 | 12/2015 | Butte et al. |

* cited by examiner

SYSTEMS AND METHODS FOR ILLUMINATING AND IMAGING

CROSS-REFERENCE

The present application is a non-provisional of, and claims the benefit of U.S. Provisional Application No. 62/296,511 filed Feb. 17, 2016; the entire contents of which are incorporated herein by reference.

BACKGROUND OF THE INVENTION

1. Field of the Invention

The present application generally relates to medical devices, systems and methods, and more particularly relates to devices, systems and methods of illuminating a surgical field or other work area.

Illuminated systems such as cameras with integrated illumination typically provide light that is concentric or coaxial with the camera image axis. The illumination element (may also be referred to herein as a source of illumination or illumination source) is often attached to or a part of the entire optical train so the illumination axis is often coaxial with the imaging axis. This may provide adequate lighting when broad general illumination of a work area such as a surgical field is needed. However, these systems may occupy too much space when more localized illumination inside of a surgical cavity is needed and the illumination element and camera are advanced closer to the work area or surgical field. Additionally, in some circumstances, when certain wavelengths of light are delivered by the light element, excessive heat may be generated and this can harm a patient, damage the camera or interfere with image quality. In still other systems, certain types of light may be delivered to the work area but the optical properties of the light may not be optimal.

It would therefore be desirable to provide improved lighting and imaging systems that can be used for either broad general lighting or for more localized illumination in tight or otherwise enclosed spaces such as a surgical field. Additionally, it would be desirable to provide improved imaging and lighting systems that can illuminate with various wavelengths of light without generating or delivering excessive heat. It would also be desirable to provide systems that can deliver light to the work area with desired optical properties. At least some of these will be satisfied by the embodiments described herein.

2. Description of the Background Art

U.S. Pat. No. 9,055,962 discloses an illuminated surgical instrument.

SUMMARY OF THE INVENTION

The present invention generally relates to medical systems, devices and methods, and more particularly relates to illumination and imaging of a surgical field.

In a first aspect, a system for illuminating a surgical field comprises a surgical imaging element such as a camera and an illumination element. The surgical imaging element may comprise an endoscope, camera, or microscope. The surgical imaging element is for imaging the surgical field and has an image axis. The illumination element is for illuminating the surgical field. The illumination element delivers light along an axis that may be coaxial or non-coaxial with the image axis of the surgical imaging element. The illumination axis may be at an angle that is the same as or different than the imaging element axis. The imaging element is preferably independently movable relative to the illumination element so that a field of view of the imaging element is adjustable while the illumination element is positionable to provide a desired amount of illumination to the surgical field. Positioning of the imaging element or the illumination may be in real time and independent of one another. Field of view may be adjusted independently of adjustment of illumination energy. Field of view may be adjusted while illumination energy is held constant.

The illumination element may comprise an optical waveguide, a fiber optic cable or one or more light emitting diodes (LEDs). The illumination element in any embodiment may include an optical component such as a lens coupled to the illumination element or a lens coupled to an optical fiber. Other exemplary illumination elements include a laser for providing laser light that may be delivered toward a target via fiber optic cable. In any embodiment herein, the illumination element may deliver or otherwise provide one or more wavelengths of light from a single source or from multiple sources. Additionally, one or more types of light may be provided by the illumination element such as speckled light and any other type of light, either of which may be supplied by a single or multiple sources of the light. Examples of types of light include different wavelengths, different intensities or energies, different sources of light, etc. Multiple sources of the light may be used concurrently in any embodiment, such as light from one or more LEDs and light from a laser. The optical waveguide may be formed into a cannula having a bore passing therethrough. The illumination element may be disposed closer to the surgical field than the camera, or the illumination element may be disposed further away from the surgical field than the camera, or the two may be at the same distance. The camera may be discrete and uncoupled from the illumination element. The illumination element may illuminate the surgical field with one or more wavelengths of light such as visible light and/or near infrared light. The illumination element may illuminate the surgical field with laser light. The illumination element may provide speckled or de-speckled light. The speckled light may be turned on or off as desired and may be provided along with other types of illumination described elsewhere in this specification.

The illumination element may comprise an optical waveguide, and the system may further comprise a laser light source. Laser light from the source may be speckled, and the speckled light may pass through the optical waveguide and exit therefrom either de-speckled or less speckled than the speckled light input into the optical waveguide. The speckled light may also be delivered via an optical fiber which may be a discrete independent fiber or bundle of fibers, or the optical fiber may be integrated into a waveguide. Light emitted from the optical waveguide may be diffuse de-speckled light, and light emitted from the optical fiber may be speckled light. In some applications the use of speckled light is desirable whereas in other applications the use of speckled light is disadvantageous. The illumination element may comprise a first or a second group of optical surface features that extract light from the illumination element and shape or otherwise control the extracted light. The system may also comprise a fluorescent dye or fluorescent marker that is disposed in the surgical field. The illumination element may excite the fluorescent dye or the fluorescent marker causing fluorescence thereof, and the camera may be configured to capture an image of the fluorescence.

The imaging element may be independently movable relative to the illumination element so that a field of view of the imaging element is adjustable while the illumination element is held in a fixed position relative to the surgical field so that the light emitted from the illumination element is held constant. Optionally, in any embodiment, the illumination element may be independently movable relative to the imaging element so that the light or other energy provided by the illumination element may be adjusted (increased, decreased, or direction of the light modified for example to control glare) while the imaging element is held in a fixed position relative to the surgical field so that the field of view of the imaging element is held constant. For example, when the illumination element is moved closer to the surgical field, brighter illumination is provided to the target without sacrificing field of view of the imaging element. In still other embodiments, both the illumination element and the imaging element may be moved together or independently of one another to adjust illumination and field of view, respectively.

In another aspect, a method for illuminating a surgical field comprises providing a surgical imaging element such as a camera having an imaging axis, providing an illumination element, and illuminating the surgical field with light from the illumination element. The illuminating comprises delivering the light along an axis that is coaxial or non-coaxial with the image axis of the surgical imaging element. The method may also comprise moving the imaging element independently of the illumination element so as to control a field of view of the imaging element while illumination energy from the illumination element is either unaffected or changed independently of the imaging field of view. The illumination element position may also be adjusted independently of the imaging element so that illumination energy is adjusted while imaging field of view is either unaffected or changed independently of the illumination energy.

The light may be delivered along the illumination axis which may or may not be coaxial with the imaging axis of imaging element. Moving the imaging element may comprise moving the imaging element independently and in real time during a surgical procedure without changing a desired amount of illumination provided to the surgical field by the illumination element. In any embodiment, it is preferable to have the illumination axis off axis relative to the imaging axis since this may reduce glare from the work area that may be reflected back to the imaging element.

Illuminating may comprise transmitting the light through the illumination element. Light may be provided by one or more light emitting diodes (LED), a waveguide employing total internal reflection, or an optical fiber. Illuminating may comprise providing light from an optical waveguide formed into a cannula with a bore extending therethrough. Any of these illumination elements may be disposed independent of camera position or the surgical imaging element. The method may further comprise disposing the illumination element closer to the surgical field than the camera. The method may also further comprise maintaining a position of the surgical imaging element that is discrete and uncoupled from the illumination element.

Illuminating may comprise illuminating the surgical field with one or more wavelengths of light such as visible light and/or near infrared light. Illuminating may comprise illuminating the surgical field with diffuse laser light or speckled laser light. The method may comprise de-speckling the light. Illuminating may comprise illuminating the surgical field with both speckled and diffuse de-speckled light.

The method may further comprise extracting the light and controlling or shaping the extracted light with a plurality of optical surface features disposed on the illumination element. The illumination element may have a first group or a first group and a second group of optical surface features with each group extracting and controlling the light differently than the other group. The method may further comprise illuminating a fluorescent dye or a fluorescent marker in the surgical field with the light, fluorescing the fluorescent dye or the fluorescent marker, and capturing an image of the fluorescence with the camera. The surgical imaging element may comprise an endoscope or a microscope and the method may comprise observing the surgical field with the endoscope or the microscope.

Moving the imaging element may comprise moving the imaging element to adjust a field of view of the imaging element while holding the illumination element in a fixed position relative to the surgical field so that the light emitted from the illumination element is held constant.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

The present invention will be described in relation to illumination of a surgical field and imaging with a camera. One of skill in the art will appreciate that this is not intended to be limiting and that the devices, systems, and methods disclosed herein may be used to illuminate any work area and that may optionally be imaged with a camera.

Figure 1:
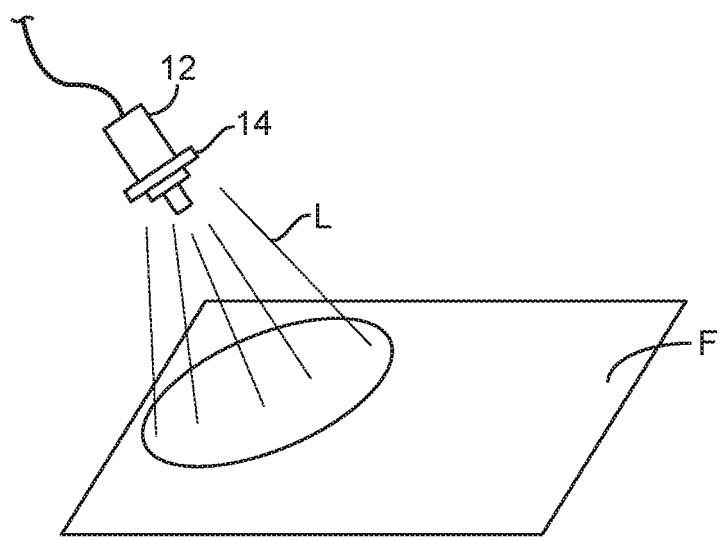
FIG. 1 illustrates coaxial illumination with a camera.

FIG. 1 illustrates a typical illuminated camera system which has a camera 12, and an illumination element 14 coupled to the camera. Light L emitted from the illumination element illuminates the work area such as a surgical field F. The light L is coaxial or concentric with the camera image axis and this system is generally used for broad surface imaging and illumination. However, the further away from the work area the light is, light intensity decreases and this can result in poor illumination of the work area. This is especially the case where the illumination is used to cause fluorescence of dyes or other markers in the work area and which are then imaged with the camera. The further the light source is from the fluorescent dye or marker, the higher the energy required to be provided by the illumination source in order to cause fluorescence and create a strong emission signal. In situations such as open surgery, ambient lighting may overpower the emitted fluorescent signal thereby making it desirable to move the camera and/or illumination element closer to the target. The closer the illumination source is to the target, the less energy is required to produce the fluorescence and create a strong emission signal. Therefore, by moving the camera with integrated light source away from the target, the camera captures a broader field of view and apparent magnification of the target is reduced, and more energy from the light source is required. Bringing the camera with integrated light closer to the target increases the energy provided by the light source to the target and may cause thermal damage to the target, but simultaneously reduces the field of view of the camera. In the exemplary embodiment where the camera and light is used with fluorescence, having the camera and light further away from the fluorescent marker allows a wider field of view but may not provide enough light to excite the marker, while bringing the camera and illumination closer to the target provides more energy to the marker to excite it but then the field of view of the camera is diminished, and potentially may crowd the working area with the camera and light. Additionally, as previously mentioned, certain wavelengths of light such as near infrared (NIR) can result in unwanted heating which can damage the system, harm the patient or result in poor image quality.

To overcome some of the challenges, the camera and illumination element may be disposed closer to the work area, and in the case of a surgical procedure, the camera may be disposed adjacent the surgical field. While this results in brighter illumination, this also provides a much narrower field of view and it may then become difficult to observe all regions of the surgical field. Additionally, the camera and illumination element may occupy a significant volume of space and this may obstruct an operator such as a surgeon from accessing the surgical field. These challenges may be solved by some of disclosure provided herein.

Figure 2A:
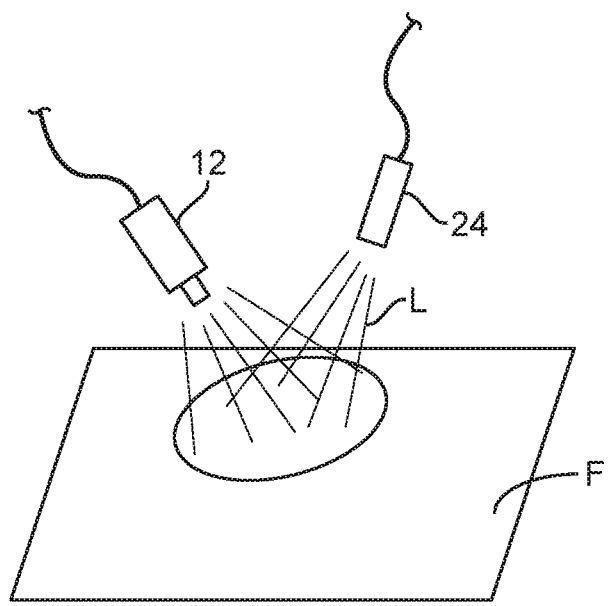
FIGS. 2A-2B illustrate off axis illumination with a camera.

Typically illumination of a target to cause fluorescence and imaging of the fluorescence is performed with the imaging element and the illumination element coaxial and co-planar. The illumination element and the imaging element are typically mounted next to one another and coupled together. FIG. 2A illustrates one exemplary embodiment of an illuminated camera system that overcomes some of the challenges described above. The illumination element 24 is separated from the camera 12, and the two components may be moved independently of one another. Therefore, the illumination element and the imaging element may be at different distances from the target and thus are not co-planar, furthermore they have different optical axes and thus may also be non-coaxial with one another. Of course the illumination element and the imaging element may in some configurations be co-planar and may be coaxial. Thus the camera may be positioned further away from the target so that a wider field of view is imaged with the camera. Additionally, the light source 24 may be positioned closer to the work area or surgical field to provide more intense light L to the surgical field F. The camera and lighting element may also be positioned anywhere around the surgical field in order to avoid obstructing access to the surgical field by the surgeon. In exemplary embodiments, the lighting element 24 may be a laser light, an optical waveguide, light emitting diodes (LEDs), fiber optics, or any other source of illumination described herein or known in the art. Thus, lighting is provided that is off axis or non-concentric with the camera image axis and the camera may be moved independently of the illumination element so that the camera or imaging element has a desired field of view, and also that the illumination element can be positioned at a desired location to provide the desired amount of light or excitation energy in the case of fluorescence. Any of the illumination elements described herein may also include optical elements such as lenses, filters, polarizers, coatings, claddings, microstructures, gratings, etc. to help provide illumination to the work area with desired illumination characteristics (such as intensity, spot size, wavelength, position, etc.). Microstructures on any of the illumination elements such as prisms, lenslets, etc. may be used to help extract, shape and direct the illumination energy such as light to a desired position in the work area or surgical field. In any embodiment, including those using an optical fiber or any other illumination element, an optical component may be included on the end of the optical fiber or on the end of an illumination element, such as a lens, or diffuser, or even a waveguide since this will provide a more uniform illumination pattern to the work area or surgical field and the emission signal of the illumination is more optimal. Any of the other optical components disclosed herein may also be used. Other exemplary illumination elements which may be included in any embodiment herein include a laser for providing laser light that may be delivered toward a target via fiber optic cable. In any embodiment, the illumination element may deliver or otherwise provide one or more wavelengths of light from a single source or from multiple sources. Additionally, one or more types of light may be provided by the illumination element such as speckled light and any other type of light, either of which may be supplied by a single or multiple sources of the light. Multiple sources of the light may be used concurrently in any embodiment, such as light from one or more LEDs and light from a laser.

Figure 2B:
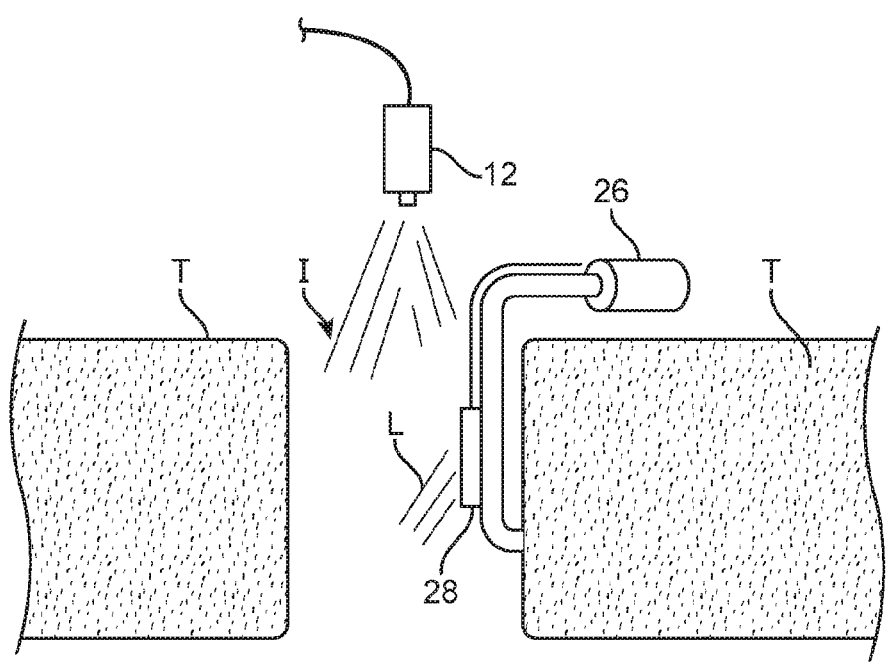

FIG. 2B illustrates another exemplary embodiment of off axis illumination, although the system may be arranged so that on axis illumination is provided. A surgical instrument such as a retractor, suction wand or other tool 26 may be disposed in an incision I through tissue T into the surgical field. An illumination element 28 such as a waveguide, LED, lights, fiber optics, etc. may be coupled or otherwise adjacent the surgical instrument 26 and therefore provides localized light L adjacent the target tissue thereby providing light with adequate energy. Any wavelength or wavelengths of light may be provided. Any of the types of illumination described herein may be delivered in this example. An adjacent camera or other instrument 12 may be positioned further away from the surgical field so that a broader field of view can be captured, thereby preventing obstruction of the surgical field with the camera. Thus the illumination element is preferably separated from the camera or other surgical instrument and illumination is provided off axis relative to the image axis of the surgical imaging element such as a camera. Optionally in this or any embodiment described herein, the light may be provided co-axially with the optical axis of the imaging element. Optionally, white light is provided by the illumination element and other wavelengths of light such as infrared light may be provided when fluorescence of target tissue is desired. Thus two or more types of light are provided by different sources of light and the two or more types of light are delivered through the same illumination element. Different types of light may comprise different wavelengths, intensities/energies, different sources of the light, as well as other characteristics used to characterize the light. As an additional example, one or more types of light may be coupled to the same illumination element to provide one or more different wavelengths of light to the target such as in the case where a white LED and laser light are used as the illumination elements. This obviates the need to disassemble the system in the middle of a procedure to install wavelength specific illumination elements. Thus, the same device may remain in the surgical field and may be used to easily provide various wavelengths of light needed for different imaging and/or illumination modalities.

Thus, an exemplary system may include an illumination element and an imaging element. The imaging element may be positioned independently of the illumination element, and the illumination element may be positioned in a desired position to provide a desired amount of illumination to the work area or surgical site, such as excitation energy in the case of fluorescence. The illumination element may provide light or energy that is coaxial or non-coaxial with the imaging element optical axis.

Figure 3:
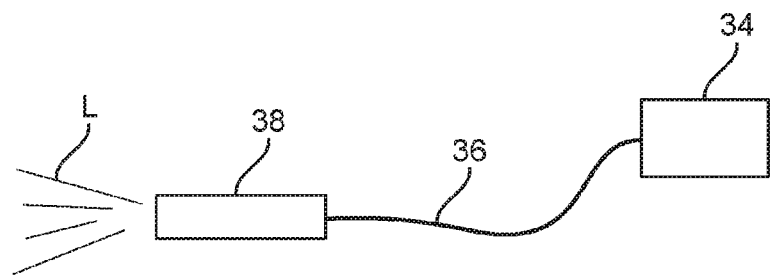
FIG. 3 illustrates an external light source coupled to an illumination element.

FIG. 3 illustrates an exemplary illumination element that may be used with the camera system in FIG. 2 or any of the embodiments disclosed herein. Illumination element 38 is coupled via a cable such as a fiber optic cable 36 to an external light source 34 such as a xenon lamp. The xenon lamp provides light which is delivered to the illumination element and the light L is emitted therefrom to illuminate the surgical field. Here the illumination element may be an optical waveguide and the xenon lamp may provide a single wavelength of light.

Figure 4:
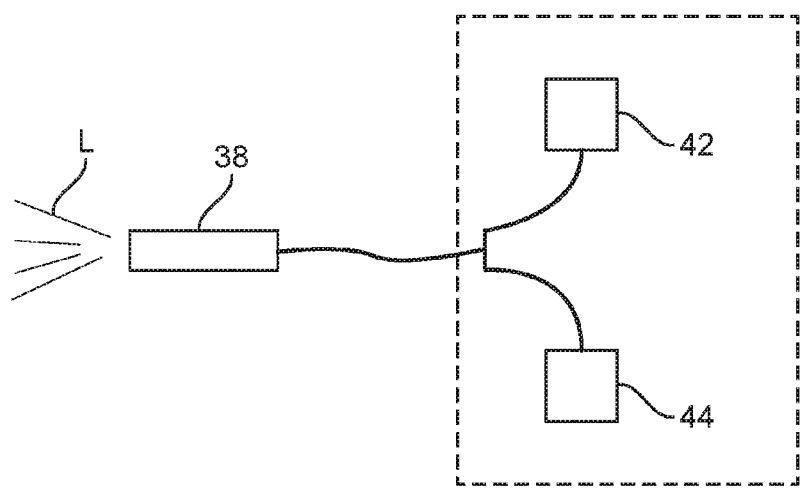
FIG. 4 illustrates multiple wavelengths of light supplied to an illumination element.

FIG. 4 illustrates a variation of the illumination element seen in FIG. 3 that may be used in any embodiment disclosed herein, with the major difference being that instead of a single source of light, the light source may comprise two or more sources of light 42, 44 so that two or more wavelengths of light may be provided to the illumination element 38. For example, one source may provide white light, while the other source may provide near infrared light (NIR). The two sources may be integrated into a single unit as indicated by the dotted line, or they may be separate units, and controls on the system may allow the user to select which frequencies of light are supplied and under what duty cycle they are supplied. Multiple frequencies of light may be advantageous since they can allow highlighting of various features. For example, white light may be provided to allow visualization of the surgical field, while another wavelength such as near infrared may be provided in order excite and cause fluorescence of dyes or other markers in the surgical field. The white light may be supplied concurrently with the infrared, or the infrared may be applied after the white light has been discontinued to prevent washout by the white light of fluorescence resulting from illumination with the infrared. Alternatively, in any of the exemplary embodiments described herein, the light source may be provided by LEDs that are disposed in the surgical field and they may provide white light, near infrared or any other desired wavelength of light or combinations of wavelengths of light in any desired order.

Figure 5:
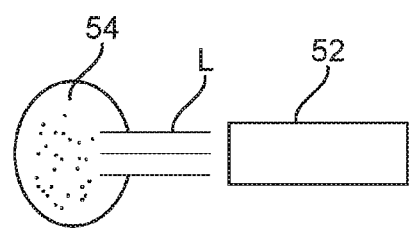
FIG. 5 illustrates laser light delivered to a work area.

FIG. 5 illustrates still another illumination element that may be used with any of the embodiments described herein. A laser 52 provides light either directly to the surgical field or the laser light may be delivered via fiber optics or an optical waveguide. When laser light is delivered directly to the surgical field, the light is typically speckled 54 due to the constructive and destructive interference within the beam of light. Speckling may be desirable or undesirable for illumination and observation purposes.

Figure 6A:
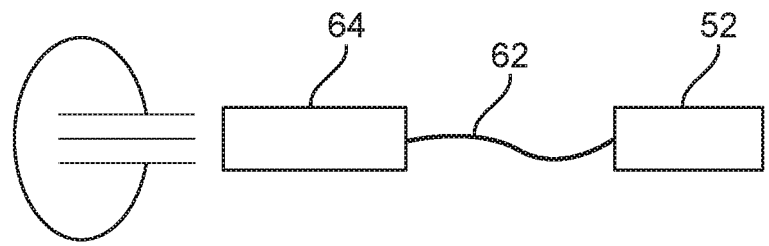
FIGS. 6A-6B illustrate laser light delivered through a waveguide.

FIG. 6A illustrates an embodiment similar to FIG. 5, with the major difference being that the light from the laser 52 is delivered either directly or indirectly via a fiber optic cable 62 into a waveguide 64. The waveguide may be any of the waveguides described herein, and may have the advantage of de-speckling the light so that it illuminates the target with less or no speckling. This may illuminate the surgical field with light having optical properties desired by the surgeon or that facilitates imaging with a camera.

Figure 6B:
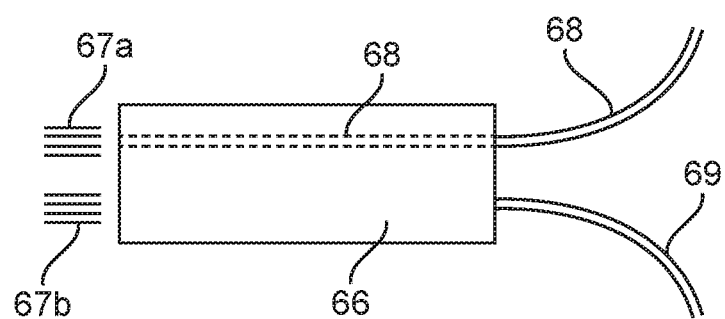

FIG. 6B illustrates a variation of the embodiment in FIG. 6A. Here, an optical waveguide 66 includes an optical fiber 68. Laser light delivered through fiber optical cable 69 into the waveguide 66 may be de-speckled by the waveguide and therefore the light 67b provided by the waveguide will be de-speckled. Light 68 supplied by fiber optic 68, if speckled, will remain speckled. It may be advantageous to provide both speckled and de-speckled light to illuminate a target. For example speckled light may be provided by a laser and used in conjunction with an imaging element such as a camera to image blood flow in a vascular structure. This is sometimes referred to as speckle contrast imaging and allows mapping and measurement of blood flow distribution in vessels. De-speckled light may be used for other imaging applications. Alternatively, it may be advantageous to provide the ability to toggle between speckled and de-speckled light. The fiber optic 68 may be disposed in a channel in the waveguide 66 or the waveguide maybe formed (e.g. injection molded) over the fiber optic. In alternative embodiments, the fiber optic 68 may be coupled to an external surface of the waveguide. The fiber optic 68 may be a single fiber or a fiber bundle. In still other embodiments, an external light source may provide light and have a de-speckling element such as a vibrating diffuser in the external light source that may be turned on or off. Thus the light from the light source may be provided either speckled or de-speckled.

Figure 7:
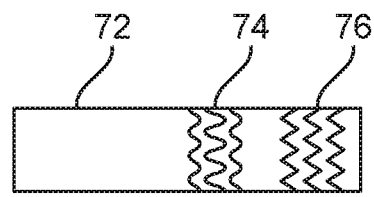
FIG. 7 illustrates an optical waveguide having light controlling structures.

Any waveguide may be used in any of the embodiments described herein. FIG. 7 illustrates an exemplary waveguide 72 that delivers light via total internal reflection. Surface features may be disposed on the waveguide to help extract and shape and control the extracted light. An optional first group of surface features 76 may be disposed on a distal surface of the waveguide to help extra light from the waveguide and direct the extracted light to the desired target such as a surgical field. The microstructures may be any form such as prisms, lensletes, or other surface features which control the light. An optional set of second microstructures 74 may be disposed near the distal end of the waveguide to shape and control extracted light from the waveguide. The first group of microstructures may be formed to shape and control a first wavelength of light, and the second group of microstructures may be formed to shape and control a second wavelength of light. The waveguide may be coupled to any instrument or hand held device such as a retractor, a suction wand, electrosurgical instrument or any other surgical instrument or tool.

Figure 8:
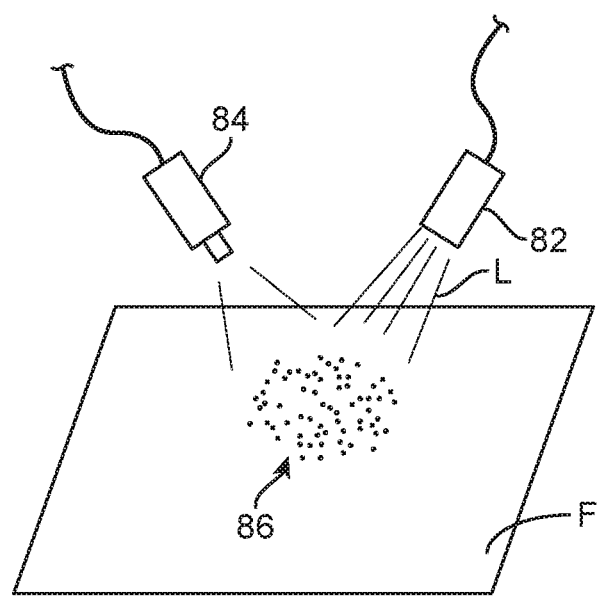
FIG. 8 illustrates an exemplary use of off axis illumination.

FIG. 8 illustrates an exemplary use of the off axis illumination described herein. Light L from an illumination element 82 is delivered to a surgical field F. The illumination element is preferably an optical waveguide but may be any of the illumination elements described herein. An external light source (not shown) provides light to the illumination element. The light L illuminates the surgical field. Dyes or other markers that bind to specific tissue targets then fluoresce 86. Camera 84 is used to image the fluorescence and the surgeon or other operator may use the camera image to help guide him either to or away from the fluorescing tissue. Because the camera is separated from the illumination element, the lighting provided is off axis or non-coaxial, non-concentric with the camera image axis. Multiple wavelengths may be provided to highlight different tissues or fluorescing markers. Thus the imaging element, here a camera may be moved independently of the illumination element to adjust its field of view, and the illumination element be adjusted independently of the imaging element to provide a desired amount of illumination, such as excitation energy in the case of fluorescence. The imaging element may have an optical axis that is coaxial with the optical axis of the illumination element, or the two may be non-coaxial. Any of the forms of illumination described herein may be delivered by the illumination element.

Figure 9A:
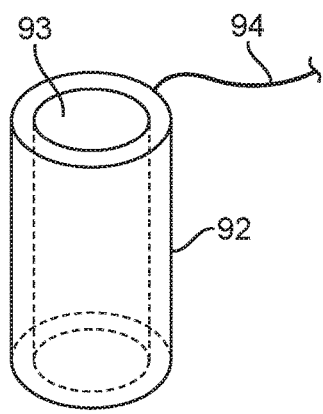
FIGS. 9A-9B illustrate use of an illuminated cannula.
Figure 9B:
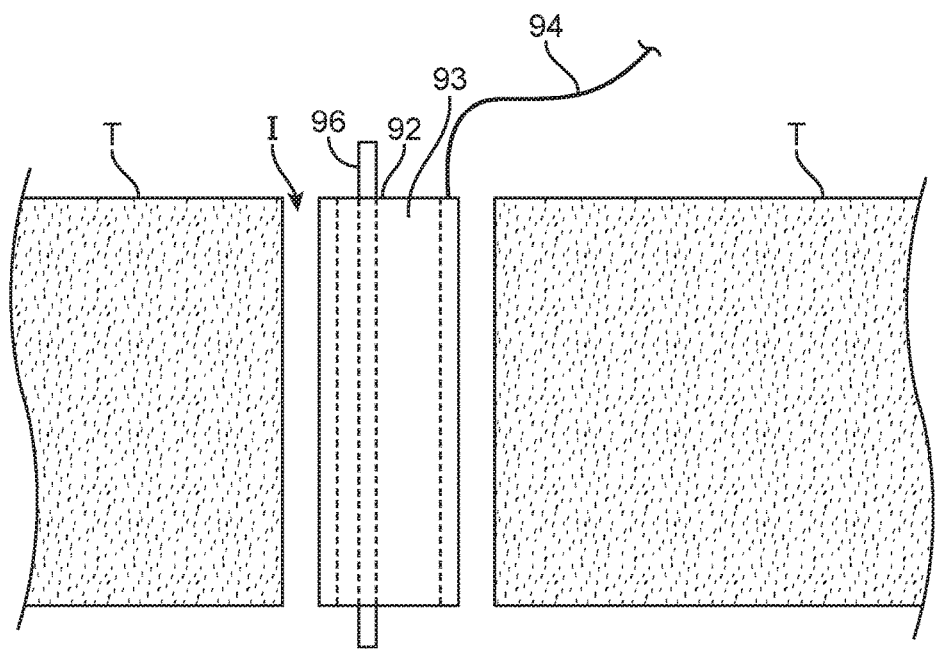

FIGS. 9A-9B illustrate use of a cannula. In FIG. 9A, a waveguide formed into a tubular cannula having a central bore 93 allows light to be delivered to a surgical field and also provides retraction of tissue away from the bore. Surgical instruments may be inserted into the bore. A fiber optic cable 94 may be coupled to the cannula so that light from an external source may be delivered to the waveguide cannula 92. The cannula 92 may be positioned in any tissue, such as cranial procedures, spinal procedures or other procedures. In addition to instruments inserted into the bore, the cannula may provide lighting so an external microscope or camera may image the surgical field through the bore, or any imaging element may be positioned in the bore, and thus the imaging axis is coaxial with the illumination axis. However this is not intended to be limiting as the imaging axis may be offset or angled relative to the illumination axis and thus the two axes may be non-coaxial. The microscope, camera or imaging element may also image outside of the bore. A single wavelength or multiple wavelengths of light may be delivered by the cannula. Any of the forms of illumination described herein may be provided by the cannula.

FIG. 9B illustrates the cannula 92 inserted into a surgical field created by an incision I in tissue T. Any surgical instrument 96 may be inserted into the bore and the cannula illuminates the surgical field with light provided by an external source or any other illumination element such as those described herein. In an exemplary embodiment, the surgical instrument 96 may be an endoscope inserted into the abdomen of a patient. Light from the waveguide illuminates the surgical field so that the surgeon can visualize the surgical field through the endoscope and thus lighting is provided that is independent of the position of the endoscope or surgical instrument. Any wavelength or wavelengths of light may be supplied by the cannula waveguide such as white light, near infrared light, etc.

Thus, in any embodiment disclosed herein, optionally, a single wavelength of light or multiple wavelengths of light may be delivered concurrently or separately. The single or multiple wavelengths of light may be provided from a single source or from multiple separate light sources. Additionally, in any embodiment disclosed herein, one type of light or multiple types of light may be delivered concurrently or separately, and they may be supplied by a single source or from multiple sources. For example, speckled light may be provided that can be delivered concurrently with another type of light or the speckled light maybe delivered and then turned off when a second type of light is delivered.

In any of the embodiments, lenslets may be used. Any of the waveguides or the lenslets may optionally comprise refractive, diffractive, or holographic structures. These structures may be used in conjunction with an appropriate wavelength of light to modify the light to have desired properties such as a specific pattern.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for illuminating a surgical field, said system comprising:
   a surgical imaging element for imaging the surgical field, the surgical imaging element having an image axis; and
   an illumination element for illuminating the surgical field,
   wherein the illumination element delivers light along an axis, and
   wherein, while the illumination element illuminates the surgical field and while the surgical imaging element is imaging the surgical field, the surgical imaging element is independently movable relative to the illumination element so that a field of view of the surgical imaging element is adjustable, and
   wherein, while the illumination element illuminates the surgical field and while the surgical imaging element is imaging the surgical field, the illumination element is independently movable relative to the surgical imaging element to adjust an amount of the light the illumination element delivers to the surgical field, and
   wherein, to adjust the amount of the light the illumination element delivers to the surgical field, the illumination element is independently movable relative to the surgical imaging element between (i) a position in which the illumination element is farther than the surgical imaging element relative to the surgical field and (ii) a position in which the illumination element is closer than the surgical imaging element relative to the surgical field,
   wherein the illumination element comprises an optical waveguide having an optical fiber disposed in the optical waveguide, and
   wherein illuminating the surgical field with the light comprises (i) emitting diffuse de-speckled light from the optical waveguide and (ii) emitting speckled light from the optical fiber.

2. The system of claim 1, wherein the axis of the illumination element is noncoaxial with the image axis.

3. The system of claim 1, wherein the illumination element is independently movable relative to the surgical imaging element while the illumination element is illuminating and while the surgical imaging element is imaging so that illumination from the illumination element is adjustable while a position of the surgical imaging element is fixed relative to the surgical field so that the field of view of the surgical imaging element remains unchanged.

4. The system of claim 1, wherein the surgical imaging element comprises a camera.

5. The system of claim 1, wherein the surgical imaging element comprises an endoscope.

6. The system of claim 1, wherein the surgical imaging element comprises a microscope.

7. The system of claim 1, wherein the illumination element comprises an optical waveguide.

8. The system of claim 1, wherein the illumination element comprises an optical waveguide formed into a cannula having a bore passing therethrough.

9. The system of claim 1, wherein the illumination element comprises a fiber optic cable or a light emitting diode.

10. The system of claim 1, wherein the illumination element is disposed closer to the surgical field relative to the surgical imaging element.

11. The system of claim 1, wherein the surgical imaging element is discrete and uncoupled from the illumination element.

12. The system of claim 1, wherein the illumination element is configured to illuminate the surgical field with a plurality of wavelengths of light.

13. The system of claim 12, wherein the plurality of wavelengths of light comprise visible light and near infrared light.

14. The system of claim 1, wherein the illumination element is configured to illuminate the surgical field with laser light.

15. The system of claim 1, wherein the illumination element is configured to provide speckled light.

16. The system of claim 1, wherein the illumination element comprises an optical waveguide, the system further comprising a laser light source, and wherein laser light from the laser light source is speckled light, and wherein the speckled light passes through the optical waveguide and exits therefrom either de-speckled or less speckled than the speckled light introduced into the optical waveguide.

17. A system for illuminating a surgical field, said system comprising:
a surgical imaging element for imaging the surgical field, the surgical imaging element having an image axis; and
an illumination element for illuminating the surgical field, wherein the illumination element delivers light along an axis, and wherein the surgical imaging element is independently movable relative to the illumination element so that a field of view of the surgical imaging element is adjustable while the illumination element is independently positionable to provide a desired amount of illumination to the surgical field,
wherein the illumination element comprises an optical waveguide having an optical fiber disposed therein, wherein light emitted from the optical waveguide is diffuse de-speckled light, and wherein light emitted from the optical fiber is speckled light.

18. The system of claim 1, wherein the illumination element comprises a first group of optical surface features for extracting light from the illumination element and shaping or otherwise controlling the light extracted from the illumination element.

19. The system of claim 18, wherein the illumination element comprises a second group of optical surface features for extracting light from the illumination element and shaping or otherwise controlling the light extracted from the illumination element.

20. The system of claim 1, further comprising a fluorescent dye or fluorescent marker disposed in the surgical field, and wherein the illumination element illuminates the fluorescent dye or the fluorescent marker causing fluorescence thereof, and wherein the surgical imaging element is configured to capture an image of a fluorescence from a fluorescent dye or a fluorescent marker illuminated by the illumination element.

21. A method for illuminating a surgical field, said method comprising:
providing a surgical imaging element having an imaging axis;
providing an illumination element;
illuminating the surgical field with light from the illumination element, wherein the illuminating comprises delivering the light along an axis;
imaging, using the surgical imaging element, the surgical field;
while the illumination element is illuminating the surgical field and while the surgical imaging element is imaging the surgical field, moving the surgical imaging element independently of the illumination element so as to control a field of view of the surgical imaging element; and
while the illumination element is illuminating the surgical field and while the surgical imaging element is imaging the surgical field, moving the illumination element independently of the surgical imaging element to adjust an amount of the light the illumination element delivers to the surgical field,
wherein the illumination element comprises an optical waveguide having an optical fiber disposed in the optical waveguide, and
wherein illuminating the surgical field with the light comprises (i) emitting diffuse de-speckled light from the optical waveguide and (ii) emitting speckled light from the optical fiber.

22. The method of claim 21, wherein the light is delivered along the axis and the axis is not coaxial with the image axis of the surgical imaging element.

23. The method of claim 21, wherein moving the surgical imaging element comprises moving the surgical imaging element in real time during a surgical procedure, without changing a desired amount of illumination provided to the surgical field by the illumination element.

24. The method of claim 21, wherein illuminating comprises transmitting the light through the illumination element by total internal reflection.

25. The method of claim 21, wherein illuminating comprises providing light from a light emitting diode or from an optical fiber.

26. The method of claim 21, wherein illuminating comprises providing light from an optical waveguide formed into a cannula with a bore extending therethrough.

27. The method of claim 21, further comprising disposing the illumination element closer to the surgical field than the surgical imaging element.

28. The method of claim 21, further comprising maintaining a position of the surgical imaging element that is discrete and uncoupled from the illumination element.

29. The method of claim 21, wherein illuminating comprises illuminating the surgical field with a plurality of wavelengths of light.

30. The method of claim 21, wherein illuminating comprises illuminating the surgical field with visible light and with near infrared light.

31. The method of claim 21, wherein illuminating comprises illuminating the surgical field with laser light.

32. The method of claim 21, wherein illuminating comprises illuminating the surgical field with speckled light.

33. The method of claim 21, further comprising de-speckling the light.

34. The method of claim 21, wherein illuminating comprises illuminating the surgical field with both speckled light and diffuse de-speckled light.

35. The method of claim 21, further comprising extracting the light and controlling or shaping the extracted light with a first group of a plurality of optical surface features disposed on the illumination element.

36. The method of claim 35, further comprising extracting the light and controlling or shaping the extracted light with a second group of a plurality of optical surface features disposed on the illumination element.

37. The method of claim 21, wherein the surgical imaging element comprises an endoscope or microscope, the method further comprising observing the surgical field with the endoscope or the microscope.

38. The method of claim 21, wherein moving the surgical imaging element comprises moving the surgical imaging element to adjust a field of view of the surgical imaging element while the illumination element is illuminating and while the surgical imaging element is imaging and while holding the illumination element in a fixed position relative to the surgical field so that the light emitted from the illumination element is held constant.

39. The method of claim 21, further comprising moving the illumination element to adjust illumination from the illumination element to the surgical field while the illumination element is illuminating and while the surgical imaging element is imaging and while holding the surgical imaging element in a fixed position relative to the surgical field so that the field of view of the surgical imaging element remains constant.

40. The method of claim 21, further comprising:
illuminating a fluorescent dye or a fluorescent marker in the surgical field with the light;
fluorescing the fluorescent dye or the fluorescent marker; and
capturing an image of the fluorescence with the surgical imaging element.

* * * * *